(12) United States Patent
Kalderon

(10) Patent No.: US 7,462,349 B2
(45) Date of Patent: Dec. 9, 2008

(54) BETA INTERFERON FOR THE TREATMENT OF CHRONIC SPINAL CORD INJURY

(76) Inventor: Nurit Kalderon, 30 River Rd., Apt. 6J, New York, NY (US) 10044

( * ) Notice: Subject to any disclaimer, the term of this patent is extended or adjusted under 35 U.S.C. 154(b) by 685 days.

(21) Appl. No.: 10/693,042

(22) Filed: Oct. 24, 2003

(65) Prior Publication Data

US 2004/0086484 A1 May 6, 2004

Related U.S. Application Data

(60) Provisional application No. 60/421,103, filed on Oct. 24, 2002.

(51) Int. Cl.
*A61K 38/00* (2006.01)
*A61K 38/19* (2006.01)
(52) U.S. Cl. .......................... 424/85.1; 514/2
(58) Field of Classification Search ................ None
See application file for complete search history.

(56) References Cited

U.S. PATENT DOCUMENTS

2003/0027755 A1 2/2003 Juan et al.

OTHER PUBLICATIONS

Ulbrich, et al, 2003, Trends in Pharmacological Science, 24(12): 640-647.*
Johnson, et al, Scientific American, May 1994, 68-75.*
L.A. Stone et al., :Characterization of MRI response to treatment with interferon beta-1b: Contrast-enhancing MRI lesion frequency as a primary outcome. Neurology, 49: 862-869, Sep. 1997.
S. Floris et al: Interferon-β directly influences monocyte infiltration into the central nervous system J. Neuroimmunology, 127: 69-79, 2002.
Kalderon N. and Fuks Z. Structural recovery in lesioned adult mammalian spinal cord by x-irradiation of the lesion site. *Proc Natl Acad Sci USA* (1996) 93: 11179-84.
Xu S., Koutcher J.A., Fuks Z., and Kalderon N. In vivo imaging (MRI) of the natural and the x-irradiation facilitated repair of the lesion in severed adult rat spinal cord, *Soc. Nuerosci. Abstr.*, (1999) 25: 493.
Xu S., Fuks Z., Koutcher J.A., and Kalderon N. The natural temporary repair of the lesion in severed adult rat spinal cord as seen in vivo by MRI, *Exp. Neurol.*, (2000) 163:295.
Xu S., Muruganandham M., Koutcher J. and Kalderon N. Progression of pathology after contusion injury in rat spinal cord: in vivo MRI studies, *Soc. Neurosci Abstr.*, (2001) 27: 2118.
Muruganandham M., Xu S., Kalderon N. and Koutcher J.A. MRI evaluation of the onset of chronic inflammation after contusion injury in rat spinal cord. *Proc. Intl. Soc. Mag. Reson. Med.*, (2002) 10.
Burrows M., Wade P.D. and Kalderon N. Critical events in the repair/decay fate of the contusion-injured rat spinal cord, *2002 Abstract Viewer/Itinerary Planner*, Washington, DC: Society for Neuroscience, Online, (2002) Program No. 133.10.
De Vries H.E., Kuiper J., De Boer A.G., Van Berkel T.J.C., and Breimer D.D. The blood-brain barrier in neuroinflammatory diseases. *Pharm Reviews* (1997) 49: 143-55.
Popovich P.G., Horner P.J., Mullin B.B. and Stokes B.T. A quantitative spatial analysis of the blood-spinal cord barrier. I. Permeability changes after experimental spinal contusion injury. *Exp Neurol* (1996) 142: 258-75.
Tator C.H. and Koyanagi I. Vascular mechanisms in the pathophysiology of human spinal cord injury. *J Neurosurg* (1997) 86: 483-492.
Mautes A.E.M., Weinzierl M.R., Donovan F. and Noble L.J. Vascular events after Spinal cord injury: Contribution to secondary pathogenesis. *Phys Ther.* (2000) 80:673-687.
C. N. Serhan et al. Resolution of Inflammation: state of the art, definitions and terms. The FASEB Journal (2007) 21:325-332.

* cited by examiner

*Primary Examiner*—Elizabeth C. Kemmerer
*Assistant Examiner*—Sandra Wegert
(74) *Attorney, Agent, or Firm*—Richard J. Sterner

(57) ABSTRACT

The invention is intended to adapt an already established clinical procedure for the treatment of multiple sclerosis (MS)—the use of beta interferon—to treat chronic human spinal cord injury. The present invention relates to the prevention of chronic inflammation and demyelination following spinal cord injury.

28 Claims, 5 Drawing Sheets

BETA INTERFERON FOR THE TREATMENT OF CHRONIC SPINAL CORD INJURY

CROSS-REFERENCE TO RELATED APPLICATIONS

This application claims the priority/benefit of U.S. Provisional Application No. 60/421,103, filed Oct. 24, 2002.

STATEMENT REGARDING FED SPONSORED R & D

This invention was partially made with government support under National Institutes of Health Grant RO1-NS 39375.

FIELD OF THE INVENTION

The present invention relates to a method for treating the secondary pathology of spinal cord injury, more particularly, using beta interferon as used for the treatment of relapsing-remitting multiple sclerosis (MS).

BACKGROUND OF THE INVENTION

Spinal cord injury (SCI) is a devastating trauma; it results in lifelong permanent neurologic deficits/disabilities. About 10,000 new major spinal injuries occur in a year in the US, the largest part in car and sports accidents, affecting mostly young males. Unlike most injuries, which result in temporary tissue damage, spinal cord injuries result in permanent tissue rupture and consequent decay. The severed nerve fibers which normally transmit the messages from the brain to the cord fail to cross the wound gap, thus leaving the cord beyond the site of injury, disconnected from the brain. The nerve cells of the cord cannot function without the messages from the brain and the related muscles become and remain paralyzed.

Mechanical injury to the spinal cord not only tears the brain-cord nerve tracts, but it also ruptures the blood vessels [Allen (1911) *J Amer Med Assoc.* 57:878-880; Balentine (1978) *Lab Invest.* 39:236-253; Mautes et al. (2000) *Phys Ther.* 80:673-687]; and the integrity of the blood brain barrier (BBB), which separates the central nervous system (brain and spinal cord) from the systemic blood circulation, is broken [Runge et al (1997) *Invest Radiol.* 32:105-110; Jaeger & Blight (1997) *Exp Neurol.* 144:381-399; Mautes et al. (2000) *Phys Ther.* 80:673-687].

It appears that the wound-repair mechanism in the spinal cord is defective [Kalderon & Fuks (1996) *Proc. Natl. Acad. Sci., USA* 93:11179-11184]; revascularization at the lesion is abnormal and the cord-blood barrier function is compromised [Loy et al. (2002) *J Comp Neurol.* 445:308-324; Popovich et al. (1996) *Exp Neurol.* 142:258-275; Jaeger & Blight (1997) *Exp Neurol.* 144:381-399]. At present it is believed that the injury to the blood vessels results in ongoing secondary damage processes that lead to progressive tissue decay at the lesion site [Tator & Fehlings (1991) *J Neurosurg.* 75:15-26; Tator & Koyanagi (1997) *J Neurosurg.* 86:483-492; Mautes et al. (2000) *Phys Ther.* 80:673-687]. A perplexing issue is whether inflammatory processes are good or bad in the pathologic outcome of SCI, as some report beneficial whereas others point to harming effects [Mautes et al. (2000) *Phys Ther.* 80:673-687].

In most cases of SCI the tissue and/or brain-cord fibers are not completely severed; nevertheless, neurologic function below the damage site is permanently lost. It has been believed that the loss of function in the intact/spared fibers is due to the secondary damage processes. It has been assumed that inflammatory processes leads, among other decay processes, to demyelination, loss of the insulating sheath of the nerve fibers that conduct messages from the brain to the cord [Blight (1991) *J Neuro. Sci.* 106:158-174; Blight (1993) *Adv Neurol.* 59:91-104; Kakulas (1999) *J Spinal Cord Med.* 22:119-124]. This loss of myelin results in loss of electrical insulation and in the "short-circuiting" of the electrical signals traveling along the affected nerve fibers with loss of neurological activity. Recent results in a rat contusion injury model show demyelination and death of oligodendrocytes, the cells that make the myelin sheath [Beattie et al. (2000) *J Neurotrauma* 17:915-925].

The working hypothesis that led to this invention is that the breakdown of the blood-cord barrier following SCI leads to chronic inflammation which is the culprit in SCI pathology. Normal wound-repair mechanisms require for the initial limited period the participation of inflammatory processes; however, persisting inflammation inevitably results in serious pathologic consequences. We have shown in longitudinal studies that the onset of chronic inflammation occurs during the 3rd week after SCI in a rat model: ex vivo by histology [Kalderon & Fuks (1996) *Proc. Natl. Acad. Sci., USA* 93:11179-11184] and in vivo by magnetic resonance imaging (MRI) [Xu et al., *Soc. Neurosci. Abstr.* (1999) 25:493; Xu et al. (2000) *Exp. Neurol.* 163:295; Xu et al., *Soc. Neurosci. Abstr.* (2001) 27:2118; Murugandham et al., *Proc Intl Soc Mag Reson Med* (2002) 10]. It is assumed that the loss of function in the intact/spared fibers is due to the secondary damage caused by the chronic inflammation which is triggered at about the 3rd week after spinal cord injury.

Multiple sclerosis (MS) is a crippling neurodegenerative disease; it is an autoimmune disease in which the person's immune system attacks its own central nervous system (i.e., brain, spinal cord and optic nerve). MS is characterized by loss of the insulating myelin sheath from around the axons of the nerve cells. This loss of myelin results in loss of electrical insulation and the "short-circuiting" of the transmission of the electrical signals along the fibers of the affected nerves resulting in progressive neurological impairment; primarily progressive paralysis. Pathologically, these self-attacks can be detected in MRI scans as sites of BBB breakdown, inflammation and/or lesion [De Vries et al. (1997) *Pharmacol Rev* 49:143-155].

A modified form of beta interferon (Betaseron®) is the first drug shown to be effective in the treatment of relapsing-remitting multiple sclerosis. Beta interferon is one of a group of immune system proteins which are produced naturally by the human body. Interferons help to regulate the immune system, and beta interferon is thought to help slow down the immune system's attack on central neural tissue, which attack leads to chronic inflammation and demyelination.

One of the interferons, interferon beta-1b (Betaseron® was approved by the Food and Drug Administration (FDA) in 1993 for treatment of relapsing-remitting MS. It was found in a clinical trial to reduce the frequency and severity of exacerbations by approximately 30%. A second interferon, interferon beta-1a (Avonex®) has also been shown to reduce the frequency and severity of MS exacerbations in people with relapsing-remitting disease. Avonex® was approved for use in MS treatment in 1996.

While the ways in which Betaseron® actually affects MS are not clearly understood, it has been demonstrated clinically that it may decrease the nerve damage associated with MS. Betaseron® has been shown to reduce the overall frequency of MS relapses, which are also called exacerbations or attacks, including the number of moderate and severe relapses. In longitudinal MRI studies Betaseron® demonstrated a strong effect in reducing BBB breakdown, reducing sites/area of chronic inflammation and in reducing lesion frequency [Stone et al. *Neurology*. (1997) 49:862-869].

VCAM-1 on blood-brain barrier endothelium is one of the major mediators of leukocyte migration through the barrier during inflammation [Engelhardt et al. (1994) *J Neuroimmunol*. 51:199-208; De Vries et al. (1997) *Pharmacol Rev* 49:143-155; Risau et al. (1998) *Patol Biol. (Paris)* 46:171-175]. Recent data in an experimental animal, in a rat MS model, suggest that beta interferon directly modulates inflammatory events at the level of cerebral endothelium [Floris et al., *J. Neuroimmun*. (2002) 127: 69-79]. It was demonstrated in that study that beta interferon treatment resulted in a marked reduction of perivascular infiltrates; this was coupled to a major decrease in the expression of the adhesion molecules ICAM-1 and VCAM-1 in brain capillaries. Further, monocyte adhesion and subsequent migration were found to be predominantly regulated by VCAM-1. These data indicate that beta interferon exerts direct anti-inflammatory effects on brain endothelial cells, thereby contributing to reduced lesion formation as observed in MS patients.

No therapies are currently available for the primary damage in spinal cord injury. Only very limited therapeutic means are currently available for spinal cord injury treatment; these are aimed at reducing the degree/extent of the secondary damage during the very early acute phases following SCI. In fact, the only generally accepted acute intervention after SCI is administration within 8 hours after injury of high doses of the steroid methylprednisolone (MP) [Bracken et al. (1990) *New Engl J Med*. 322:1405-1411; Bracken (2000) *J Neurosurg*. 93:175-179]. However, after 13 years of experience this treatment is still quite controversial, and several recent studies suggest that treatment with MP may actually be contraindicated [Hurlbert (2000) *J Neurosurg*. 93:1-7; Pointillart et al. (2000) *Spinal Cord* 38:71-6].

No therapies are currently available for either the primary or the secondary damage in chronic SCI. Also, preclinical and clinical studies and published inventions and applications for inventions that are focused on development of therapies and interventions for SCI are devoted exclusively on the early phases, within several hours up to about a week, after SCI [for example, US patent application 20030027755, published Feb. 6, 2003].

Our preliminary data, in a rat spinal cord contusion injury model, show that chronic inflammation at the lesion site is triggered, at the molecular level, only by the end of the 2nd and/or 3rd week after injury. Our data show that following injury the expression of VCAM-1 on cord endothelial cells starts to increase above background levels only by the end of the 2nd week and/or 3rd week and that it becomes expansive throughout the lesion site by the 4th week postinjury [Burrows, et al., (2002) Program No. 133.10., 2002 *Abstract Viewer/Itinerary Planner*. Washington, D.C.: Society for Neuroscience, Online]. Based on our observations, it is anticipated that beta interferon would suppress the pathologic enhanced expression of VCAM-1 following spinal cord injury in the same manner it does in experimental models of MS. It is anticipated that beta interferon would gain access to the lesion site via the leaky BBB and would exert its physiological function, inhibiting thereby the chronic inflammation and demyelination and thus leading to rescue of neurologic function of the spared, uninjured spinal cord tissue including the spared brain-cord fiber tracts.

ADVANTAGES AND SUMMARY OF THE INVENTION

A principal objective of the present invention is to provide a novel and effective treatment for chronic spinal cord injury.

A principal objective of the present invention is to provide a novel and effective treatment for reducing the progressive secondary damage in chronic spinal cord injury.

The present invention provides a method for attenuating and/or preventing the chronic inflammation that prevails at the lesion site of injured spinal cord which comprises the use of an existing clinical drug-treatment that was already proven to be effective in containing/preventing chronic inflammation in central neural tissues such as brain and spinal cord.

The present invention provides a method for attenuating and/or preventing the chronic inflammation that prevails at the lesion site of injured spinal cord which comprises administering an effective amount of beta interferon as used for the treatment of MS.

The present invention provides a method for therapy and rescue of the uninjured neuronal fiber tracts in chronic spinal cord injuries which comprises administering an effective amount of beta interferon as used for the treatment of MS.

The present invention provides a method for repair and rescue of the neurologic function of the uninjured neuronal fiber tracts in chronic spinal cord injuries which comprises administering an effective amount of beta interferon as used for the treatment of MS.

DETAILED DESCRIPTION OF THE INVENTION

I. Definitions

Figure 1:
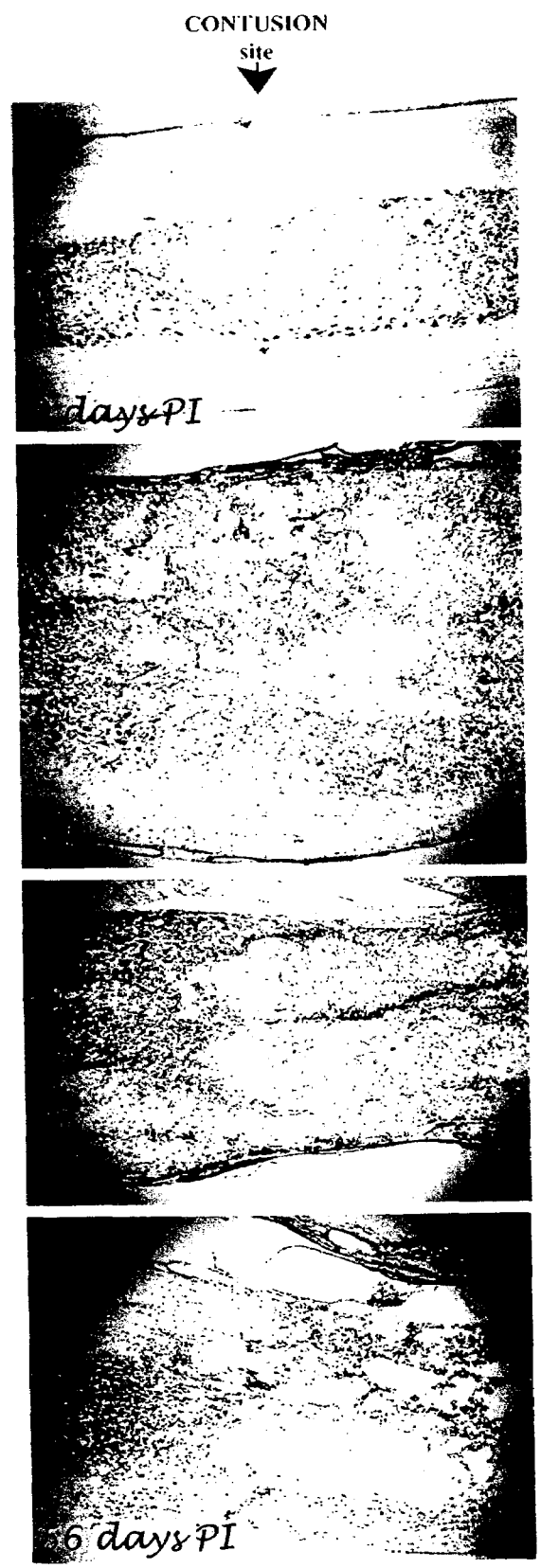
FIG. 1 shows the longitudinal progression of pathology at the lesion site following contusion injury: an ex vivo view.

Unless defined otherwise, all technical and scientific terms used herein have the same meaning as commonly understood by one of ordinary skill in the art to which this invention belongs. The following terms have the meaning indicated:

"SCI" as used herein refers to traumatic injuries sustained to the spinal cord and the area around it. This includes contusion and/or compression injuries, as well as transection injury. The model used in the studies demonstrating the utility of this invention is contusion, which is most similar to the common types of SCI sustained by humans, such as injuries sustained in motor vehicle accidents and/or sports-related injuries. [SCI is characterized by sudden loss of complete or partial motor function, the extent of which depends on the location of the injury. Higher (cervical) injuries can result in total loss of motor function or quadriplegia and loss of respiratory control, and sometimes cardiovascular collapse. Lower lesions (thoracic) can result in paraplegia but without arm involvement or respiratory dysfunction.]

"BBB" as used herein refers to both barriers, the barrier between the blood and the brain and the barrier between blood and the spinal cord.

Utility of the Invention

This invention is intended to treat chronic human spinal cord injury. The invention is intended to adapt an already established clinical procedure for the treatment of the neurodegenerative disease multiple sclerosis (MS)—the use of beta interferon—to treat chronic human spinal cord injury. The basis for the invention is the unexpected (counterintuitive) discovery that the underlying/crucial event leading to the pathologic hallmarks of spinal cord injury and MS are identical; in both it is the breakdown of the BBB. The primary cause of MS, the autoimmune trigger, is unknown; however, the BBB breakdown is a consequence of the autoimmune response to the self central neural components [DeVries et al. (1997) *Pharmacol Rev* 49:143-155; Pachter et al. (2003) *J Neuropathol Exp Neurol.* 62:593-604] In SCI the BBB breakdown is due to the injury to the spinal cord blood vessels. Once the BBB is broken, both in SCI and in MS, chronic inflammation ensues resulting in tissue degenerative processes, such as demyelination. As discussed above, it was demonstrated in clinical trials in MS patients and in an animal MS model that chronic inflammation can be contained/prevented by treatment with beta interferon, suggesting a direct effect on VCAM-1 levels (reduction). Since the underlying event leading to chronic inflammation in chronic SCI has now been found to be identical to the event in MS, the present invention is directed to beta-interferon treatment to prevent chronic inflammation and its devastating consequences in chronic SCI.

To demonstrate the utility of the invention, chronic inflammation and its onset following SCI were characterized and determined in longitudinal studies, by histology, by in vivo MRI and by immunohistology for VCAM-1 levels. These studies were performed in a contusion injury model that is similar to the human SCI. A moderate contusion injury was performed in adult female rat using an NYU weight-drop device which generates a reproducible degree of injury, structural and functional [Gruner, J. A, *J. Neurotrauma* (1992), 9:123-6; Basso et al. (1996) *Exp Neurol.* 139:244-256].

The analysis suggests chronic inflammation associated with SCI is an ongoing process at the site of lesion that can be stopped/attenuated by treatment with beta interferon. Preferably, the treatment should start at about the 11th day after injury when the decay is triggered, but it can be applied months or even years after injury to rescue the spared tissue from further degeneration.

EXAMPLES

Example 1

Onset of Tissue Degradation at the 4th Week After Injury: by Histology

The progression of events at the lesion site after contusion injury in adult rat spinal cord was studied. A moderate thoracic contusion was performed with an NYU weight-drop device. The lesion site in sagittal sections was analyzed at 0, 4, 6, 8, 11, 14, 19, 21, 28, 34, 40, 50 and 56 days postinjury (PI) by routine histology as described previously [Kalderon & Fuks 1996]; some of the temporal events are shown in FIG. 1. This figure is a composite of light photographs of histologically stained (thionin) sagittal rat spinal-cord sections at different time points after injury, at 0, 11, 21, and 56 days postinjury (PI). During the first 2 weeks PI only small regions at the lesion epicenter appear to be abnormal; signs of an extensive tissue disintegration can be seen at the end of the 3rd week (21 days) and cavitation with continued tissue decay is seen at about 2 months (56 days) PI.

The Data show that, apart from the swelling which develops by the 4th day PI [not shown], the progression of events after contusion is similar to that in transection injury [Kalderon & Fuks (1996) *Proc. Natl. Acad. Sci., USA* 93:11179-11184]. That is, wound repair seems to proceed through the 2nd week PI whereas early signs of tissue decay/disintegration are detected at the 4th week PI. Tissue decay is an unremitting process, seen as a cavitation at the lesion site that is expanding with time after injury.

Example 2

Onset of Chronic Inflammation During 3rd Week After Injury: In Vivo MRI

Figure 2:
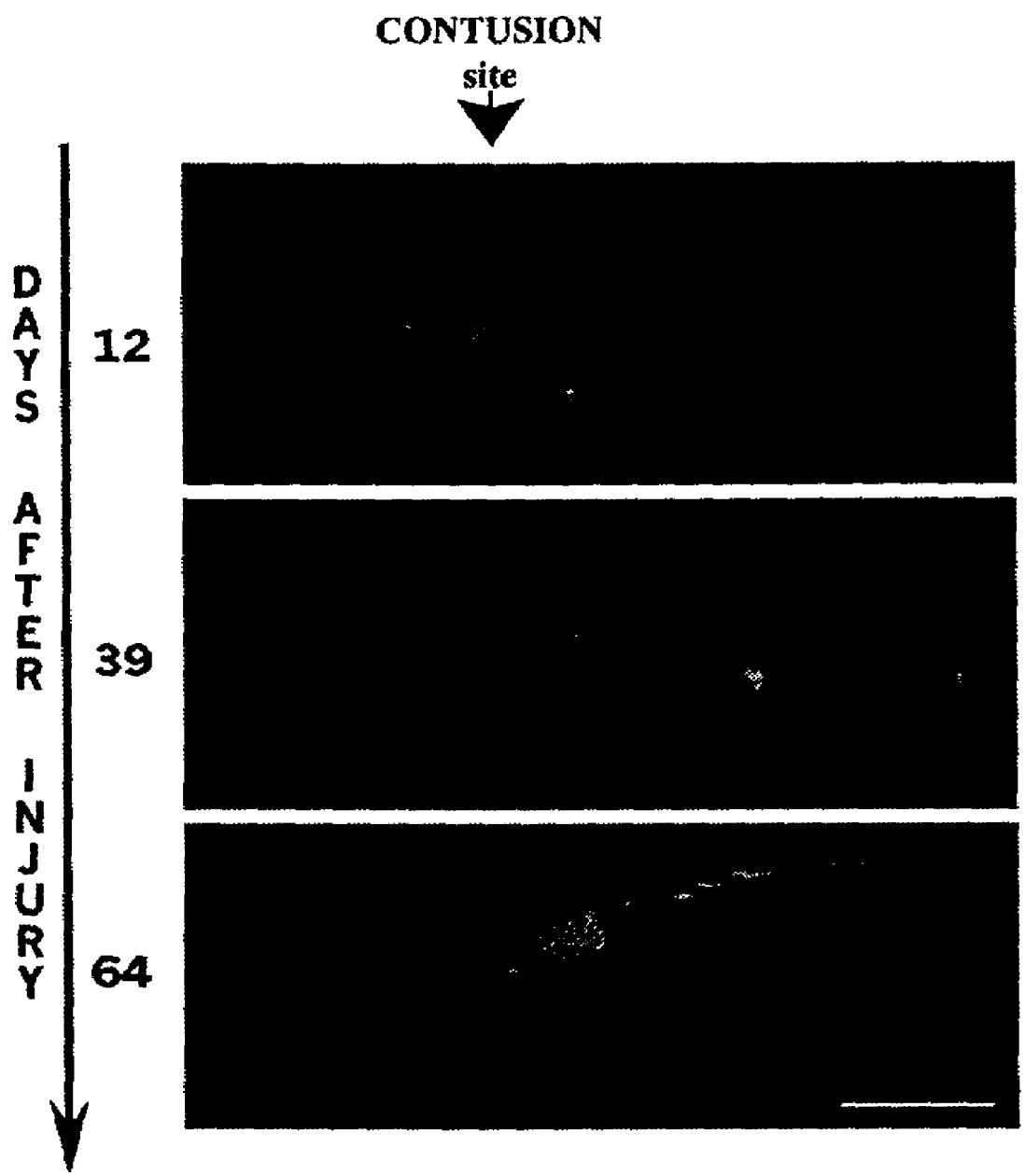
FIG. 2 shows the onset and progression of chronic inflammation following contusion injury: an in vivo MRI view.

In another study we obtained by MRI a dynamic in vivo view of the progression of events at the lesion site after contusion injury. MRI scans of the lesion site at the spinal cord were obtained on a 4.7T/33 cm bore CSI Omega imaging spectrometer (Bruker, Fremont, Calif.) equipped with shielded gradients (7 G/cm) and a 30×30 mm square homemade surface coil while the rat was anaesthetized. The spinal cords of adult Sprague-Dawley female rats (n=10), 3-6 months old were contused above the waist (low thoracic level). Using a spin echo sequence, $T_2$-weighted sagittal (FIG. 2) and axial images (not shown) of the lesion site were acquired at different time intervals within 6-42 days PI [Murugandham et al., *Proc. Intl Soc Mag Reson Med.* (2002) 10]. FIG. 2 is a composite of $T_2$-weighted MRI sagittal images of the lesion site of a contused rat spinal cord that were taken in vivo at 3 time points, at 12, 39 and 63 days after injury. By the end of the 2nd week (12 days) postinjury the spinal cord seems to be almost normal with very little evidence of the initial lesion; the onset of chronic inflammation is depicted at the center as an hyper-intense focal signal. at day 12 covering almost a cord by PI. A month later (day 39), the area of chronic inflammation (hyper-intense signal) is extensive, covering almost a cord segment (6 mm) and by day 64 PI the cord has shrunk and chronic inflammation remains extensive. Bar=5 mm.

The progression of events as seen in vivo indicates that the 1st week PI is marked by edema and enlargement of the central canal. During the 2nd week PI all obvious signs of trauma dissipate, suggesting repair. Onset of the chronic inflammation occurs through the 3rd week PI, observed as pointed hyper-intense signal localized at the cord center, and this flares up by the 4th week PI [FIG. 2]. At the 2nd month PI, inflammation and tissue decay prevail at the lesion site spreading from the epicenter radially and laterally covering a segment of 5-10 mm long while the cord shrinks.

Example 3

Onset of Chronic Inflammation at the BBB: Rise In VCAM-1 Levels in Barrier Endothelia.

VCAM-1 on blood-brain barrier endothelium is one of the major mediators of leukocyte migration through the barrier during inflammation. We quantitatively pinpointed the onset of chronic inflammation at the lesion site after contusion-injury in rat spinal cord (0, 4, 6, 8, 11, 14, 19, 21, 28, 34, 40, 50 & 56 days PI) using VCAM-1 immunocytochemistry [Kalderon et al. (1990) *Proc Natl Acad. Sci. USA* 87:10058-10062]. These data are summarized in FIGS. 3-5. Immediately after injury (0 days) the levels of VCAM-1-labeled cells at the lesion site significantly declined (p=0.01); these levels returned to normal levels by day 4-6 PI. Significant increase (p=0.05), above normal levels, in VCAM-1-expressing cells occurred during the 3rd week PI. The rise in VCAM-1 was first noticed on day 11 PI; by day 14 it was twice the normal levels, and flaring up (3-times the normal level) by day 19-21 PI was seen as a continuous band of several cell layers that is surrounding the lesion site (FIGS. 4-5).

Figure 3:
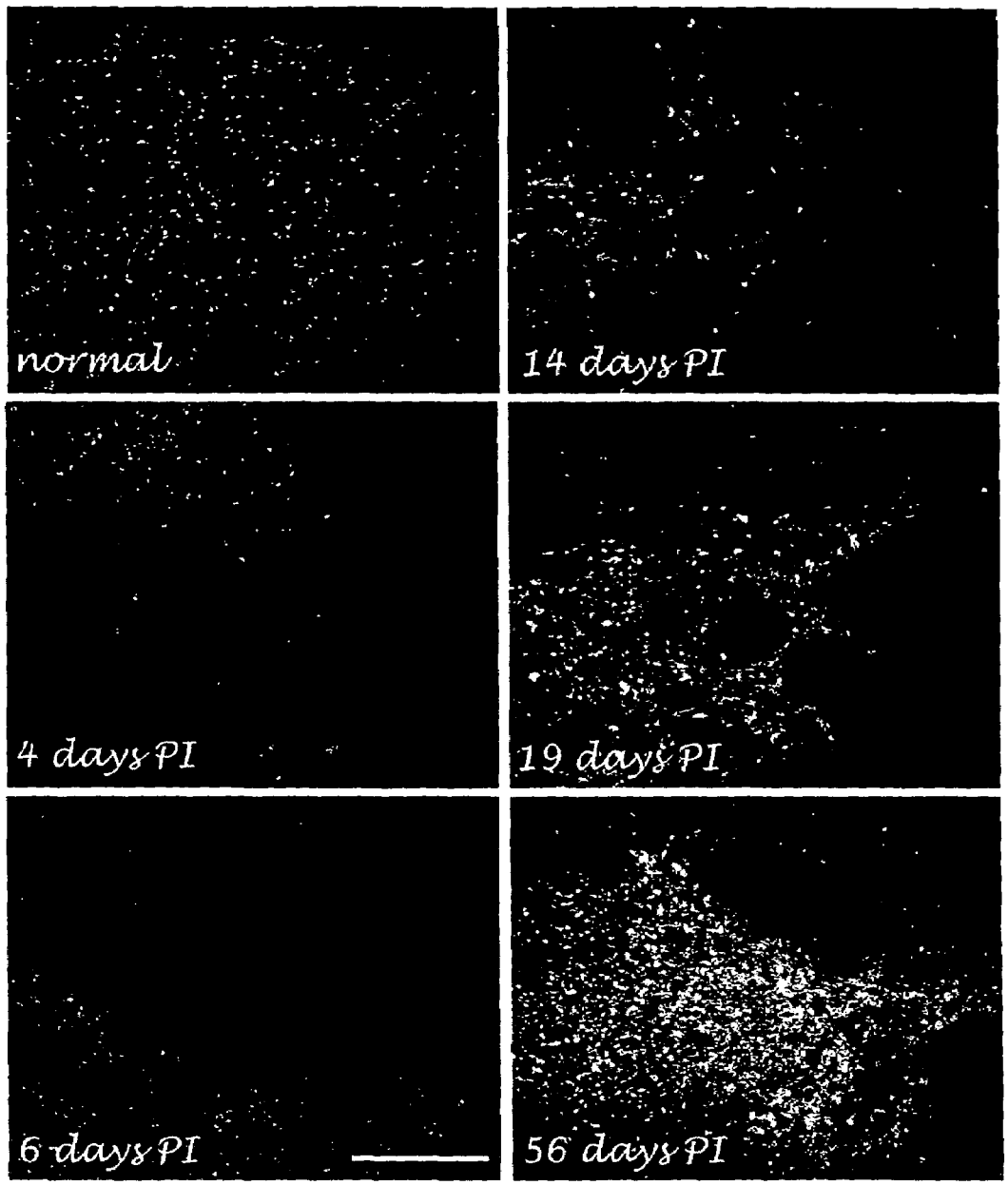
FIG. 3 shows the progression of pathology at the blood-spinal cord barrier seen with VCAM-1 following contusion injury via a longitudinal temporal view of VCAM-1-positive cells at the lesion site.

FIG. 3 is a composite of fluorescent micrographs of sagittal rat spinal-cord sections, normal and contused at different time points (4, 6, 14, 19 & 56 days) PI, in which VCAM-1-positive cells were identified by indirect immunostaining. In the 1st week PI the lesion site is devoid of any VCAM-1 labeling. A significant increase in level and distribution of VCAM-1-positive cells that differs from that of the normal is seen during the 3rd week (day 19) PI. By the 2nd month (day 56) PI the lesion site is "on fire" showing a very extensive presence of activated endothelial cells (VCAM-1-expressing cells). Bar=0.25 mm.

Figure 4:
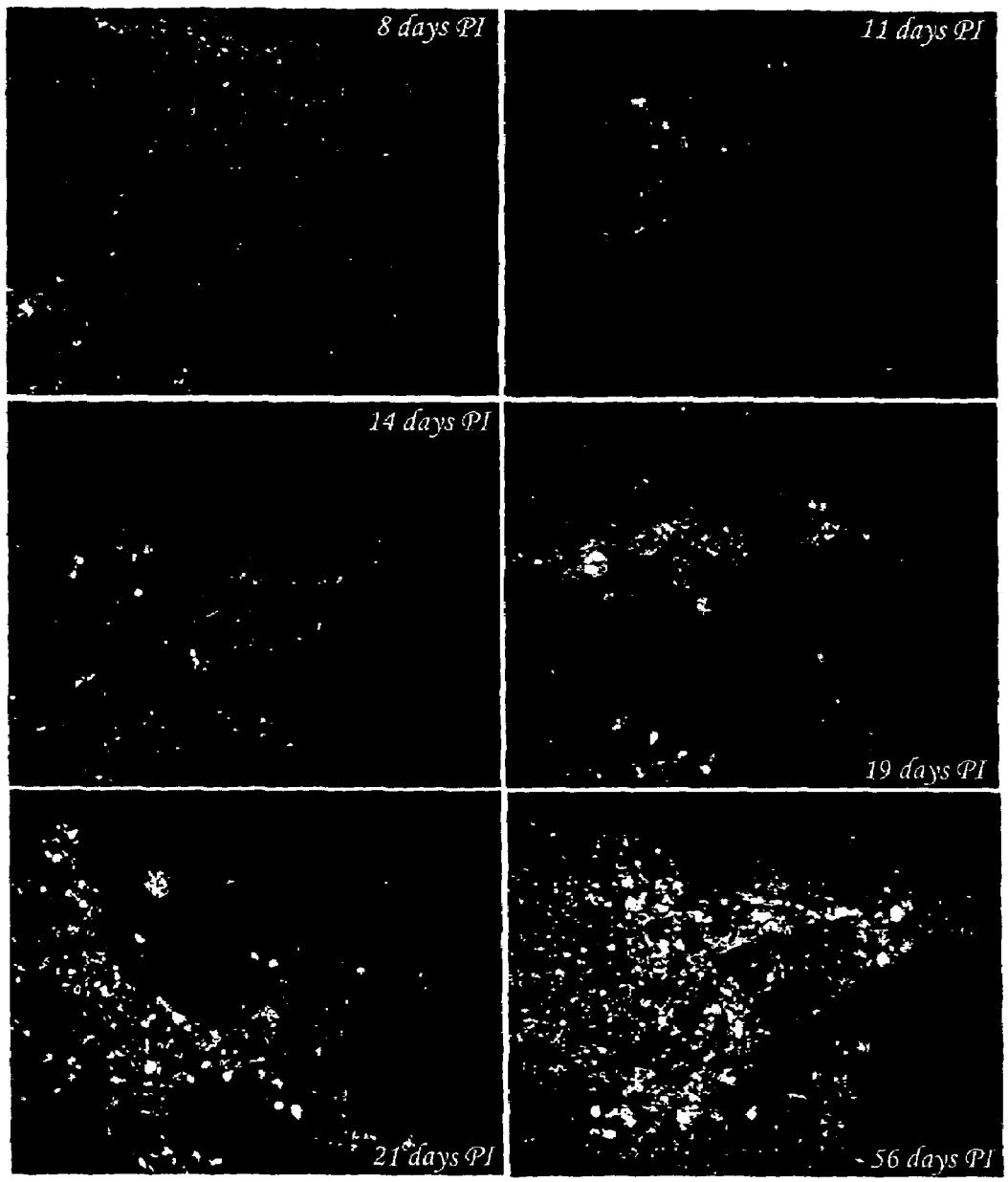
FIG. 4 shows the onset of chronic inflammation in contusion injury at the blood-spinal cord barrier via a longitudinal temporal view of VCAM-1-positive cells at the lesion site following contusion.

FIG. 4. is a composite of fluorescent micrographs of sagittal contused rat spinal-cord sections taken at different time points (8, 11, 14, 19, 21, & 56 days) PI, in which VCAM-1-positive cells were identified by indirect immunostaining. In the 1 st week PI (day 8) the lesion site is devoid of any VCAM-1 labeling; during the 2nd week (days 11&14) PI the lesion site is vascularized with a few VCAM-1-positive cells, suggesting ongoing wound repair. Onset of inflammation is depicted during the 3rd week (day 19) PI. This flaring up by day 21 PI is seen as a band composed of several cell layers surrounding the lesion site.

Figure 5:
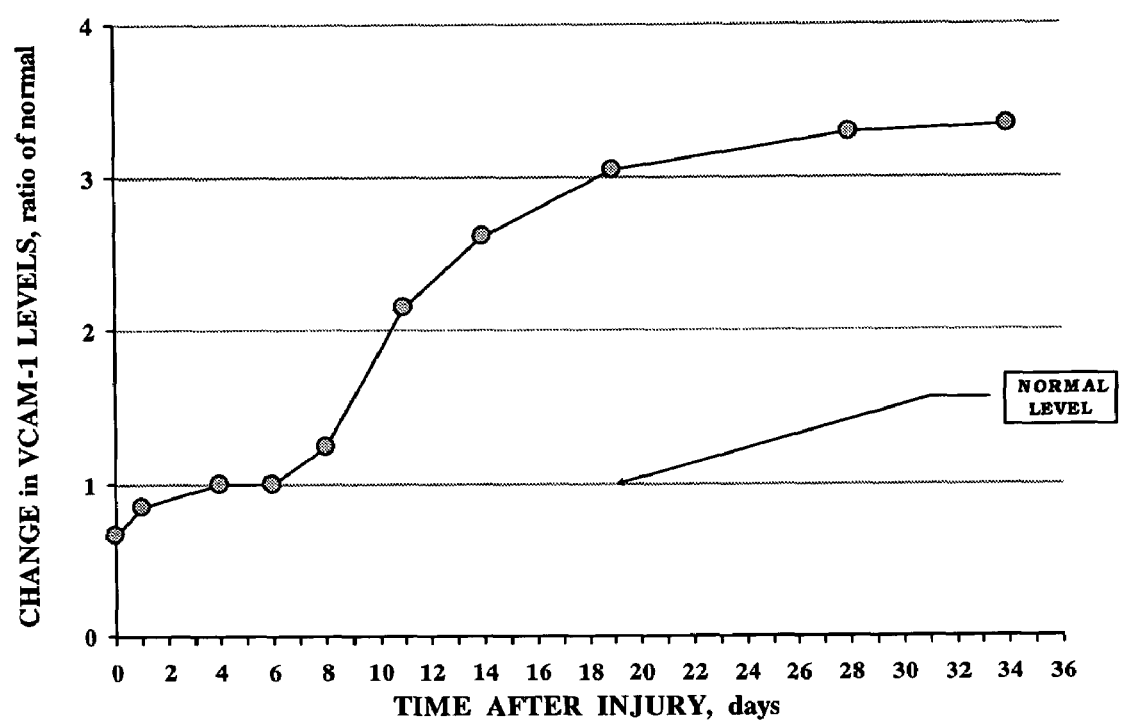
FIG. 5 shows the onset of chronic inflammation in contusion injury at the blood-spinal cord barrier: quantitative determination.

FIG. 5 is a graph displaying the results of the quantitative determination of the changes in levels of VCAM-1-expressing cells at and around the lesion site following contusion injury at 0, 1, 4, 6, 8, 11, 14, 19, 28, 34 days PI. Quantitative morphometric analysis was performed in 3 different spinal cords for each time point and in 3 different sections for each cord using Image ProPlus software. Following injury the levels of VCAM-1-labeled cells significantly declined (p=0.01), these levels returning to normal levels by day 4-6 PI. Significant increase (p<0.05), above normal levels, in VCAM-L-expressing cells was seen on day 11 PI; this time point is viewed as the time of onset of chronic inflammation. Statistics, 2-tailed t-test.

The data of the changes in VCAM-1 levels corroborate/correlate with the data obtained in the in vivo MRI study in which pointed inflammation was first noticed early in the 3rd week PI, flaring up a week later and expanding with time PI. Since VCAM-1 is a protein which controls the pathway of inflammation, it is a more sensitive/accurate criterion than MRI for detecting the onset of chronic inflammation. Altogether, it appears that the switch from repair to decay occurs during day 10-14 after injury. It also appears that in the same manner that treatment with beta interferon effectively reduces the lesions seen by MRI in MS patients and prevents the expression of VCAM-1 in the MS rat model treatment with beta interferon should also bring to good health the spared brain-cord fibers in chronic SCI victims.

What is claimed is:

1. A method for treating the secondary damage resulting from spinal cord injury, which comprises administering to a subject in need thereof a therapeutically effective amount of beta interferon or an analogue thereof.

2. The method as recited in claim 1, wherein the beta interferon or analogue thereof is commercially available and is approved by the FDA for the treatment of multiple sclerosis (MS).

3. The method as recited in claim 2, wherein the beta interferon or analogue thereof is administered as prescribed for the treatment of MS.

4. The method as recited in claim 1, wherein the beta interferon or analogue thereof is Betaseron, Avonex, Rebif or Cinnovex.

5. The method as recited in any one of claims 2-4, wherein the commercially available beta interferon is administered at the dosage and frequency as prescribed for the treatment of relapsing-remitting MS.

6. The method as recited in claim 5, wherein the beta interferon is administered starting at about the 11th day or later after injury.

7. The method as recited in claim 5, wherein the beta interferon is administered starting at the 4th week or later after injury.

8. A method of attenuating the progressive chronic inflammation and demyelination resulting from spinal cord injury, which comprises administering to a subject in need thereof a therapeutically effective amount of beta interferon or an analogue thereof.

9. The method as recited in claim 8, wherein the beta interferon or analogue thereof is commercially available and is approved by the FDA for the treatment of MS.

10. The method as recited in claim 9, wherein the beta interferon or analogue thereof is administered as prescribed for the treatment of MS.

11. The method as recited in claim 8, wherein the beta interferon or analogue thereof is Betaseron, Avonex, Rebif or Cinnovex.

12. The method as recited in any one of claims 9-11, wherein the commercially available beta interferon is administered at the dosage and frequency as prescribed for the treatment of relapsing-remitting MS.

13. The method as recited in claim 12, wherein the beta interferon is administered starting at about the 11th day or later after injury.

14. The method as recited in claim 12, wherein the beta interferon is administered starting at the 4th week or later after injury.

15. A method for therapy and rescue of the uninjured neuronal fiber tracts in chronic spinal cord injuries, which comprises administering to a subject in need thereof a therapeutically effective amount of beta interferon or an analogue thereof.

16. The method as recited in claim 15, wherein the beta interferon or analogue thereof is commercially available and is approved by the FDA for the treatment of MS.

17. The method as recited in claim 16, wherein the beta interferon or analogue thereof is administered as prescribed for the treatment of MS.

18. The method as recited in claim 15, wherein the beta interferon or analogue thereof is Betaseron, Avonex, Rebif or Cinnovex.

19. The method as recited in any one of claims 16-18, wherein the commercially available beta interferon is administered at the dosage and frequency as prescribed for the treatment of relapsing-remitting MS.

20. The method as recited in claim 19, wherein the beta interferon is administered starting at about the 11th day or later after injury.

21. The method as recited in claim 19, wherein the beta interferon is administered starting at the 4th week or later after injury.

22. A method for repair and rescue of the neurologic function of the uninjured neuronal fiber tracts in chronic spinal cord injuries, which comprises administering to a subject in need thereof a therapeutically effective amount of beta interferon or an analogue thereof.

23. The method as recited in claim 22, wherein the beta interferon or analogue thereof is commercially available and is approved by the FDA for the treatment of MS.

24. The method as recited in claim 23, wherein the beta interferon or analogue thereof is administered as prescribed for the treatment of MS.

25. The method as recited in claim 22, wherein the beta interferon or analogue thereof is Betaseron, Avonex, Rebif or Cinnovex.

26. The method as recited in any one of claims 23-25, wherein the commercially available beta interferon is administered at the dosage and frequency as prescribed for the treatment of relapsing-remitting MS.

27. The method as recited in claim 26, wherein the beta interferon is administered starting at about the 11th day or later after injury.

28. The method as recited in claim 26, wherein the beta interferon is administered starting at the 4th week or later after injury.

* * * * *